US00RE40360E

(19) United States
(12) Reissued Patent
D'Amato

(10) Patent Number: US RE40,360 E
(45) Date of Reissued Patent: *Jun. 3, 2008

(54) METHODS FOR INHIBITION OF ANGIOGENESIS WITH A COMPOSITION COMPRISING 3-HYDROXYTHALIDOMIDE

(75) Inventor: Robert J. D'Amato, Lexington, MA (US)

(73) Assignee: The Children's Medical Center Corporation, Boston, MA (US)

( * ) Notice: This patent is subject to a terminal disclaimer.

(21) Appl. No.: 11/384,188

(22) Filed: Mar. 17, 2006

Related U.S. Patent Documents

Reissue of:
(64) Patent No.: 5,712,291
Issued: Jan. 27, 1998
Appl. No.: 08/468,792
Filed: Jun. 6, 1995

U.S. Applications:
(63) Continuation of application No. 08/168,817, filed on Dec. 15, 1993, now Pat. No. 5,629,327, which is a continuation-in-part of application No. 08/025,046, filed on Mar. 1, 1993, now abandoned.

(51) Int. Cl.
*A61K 31/445* (2006.01)

(52) U.S. Cl. ..... 514/323; 514/557; 514/625; 514/417

(58) Field of Classification Search ..... 514/323, 514/557, 625, 417
See application file for complete search history.

(56) References Cited

U.S. PATENT DOCUMENTS

| | | | | | |
|---|---|---|---|---|---|
| 2,830,991 | A | * | 4/1958 | Keller et al. | 546/200 |
| 3,560,495 | A | * | 2/1971 | Frankus et al. | 544/130 |
| 3,563,986 | A | * | 2/1971 | Frankus et al. | 544/130 |
| 3,625,946 | A | * | 12/1971 | Koch et al. | 546/200 |
| 3,705,162 | A | * | 12/1972 | Grandums et al. | 546/187 |
| 4,552,888 | A | * | 11/1985 | Koppel et al. | 514/474 |
| 4,808,402 | A | * | 2/1989 | Leibovich et al. | 424/423 |
| 4,994,443 | A | * | 2/1991 | Folkman et al. | 514/56 |
| 5,001,116 | A | * | 3/1991 | Folkman et al. | 514/56 |
| 5,021,404 | A | * | 6/1991 | Folkman et al. | 514/26 |
| 5,134,127 | A | * | 7/1992 | Stella et al. | 514/58 |
| 5,260,329 | A | * | 11/1993 | Mongelli et al. | 514/422 |
| 5,593,990 | A | | 1/1997 | D'Amato | |
| 5,629,327 | A | * | 5/1997 | D'Amato | 514/323 |
| 5,635,517 | A | * | 6/1997 | Muller et al. | 514/323 |
| 5,712,291 | A | | 1/1998 | D'Amato | |
| 6,071,948 | A | | 6/2000 | D'Amato | |
| 6,114,355 | A | | 9/2000 | D'Amato | |
| 6,228,879 | B1 | | 5/2001 | D'Amato | |
| 6,235,756 | B1 | | 5/2001 | D'Amato | |
| 6,420,414 | B1 | | 7/2002 | D'Amato | |
| 6,469,045 | B1 | | 10/2002 | D'Amato | |
| 6,518,298 | B2 | | 2/2003 | D'Amato | |
| 6,977,268 | B2 | | 12/2005 | D'Amato | |
| 2002/0161023 | A1 | | 10/2002 | D'Amato | |
| 2002/0161024 | A1 | | 10/2002 | D'Amato | |
| 2003/0176463 | A1 | | 9/2003 | D'Amato | |
| 2003/0181428 | A1 | | 9/2003 | D'Amato | |
| 2003/0187024 | A1 | | 10/2003 | D'Amato | |
| 2005/0004087 | A1 | | 1/2005 | D'Amato | |

FOREIGN PATENT DOCUMENTS

| | | | |
|---|---|---|---|
| EP | 0325199 | * | 7/1989 |
| EP | 0357061 | * | 3/1990 |
| GB | 1182709 | * | 3/1970 |
| JP | 58-131978 | * | 8/1983 |
| JP | 63-119500 | * | 5/1988 |
| WO | WO 92/14455 | * | 9/1992 |
| WO | WO 92/18496 | * | 10/1992 |

OTHER PUBLICATIONS

Boylen, "Tetratogenic Effects . . . ", Can. J. Biochem, vol. 42, pp. 35–42, 1964.*
Mujagid, "Mechanisms of Action and potential . . . ", Coration Medical Journal, vol. 43 No. 3, pp. 274–285, 2002.*
Rajumar, Mayo Clin Proc, Jul. 2004, vol. 79(7), pp. 899–903.*
Kumar, J Clin Oncol, vol. 22(12), Jun. 2004, pp. 2477–2488.*
Singhal, Biomed Pharmacother, vol. 56, 2002, pp. 4–12.*
Thomas, Curr Opin Oncol, vol. 12, pp. 564–573, 2000.*
Glasmacher, Acta Haematol, vol. 114 (suppl 1), pp. 3–7, 2005.*
Diggle, IJCP, Nov. 2001, vol. 55 (9), pp. 627–631.*
Ribatti, Leukemia, vol. 19, pp. 1525–1531, 2005.*
D'Amato, Proc Natl Acad Sci USA, vol. 91, pp. 4082–4085, Apr. 1994.*
Moses, Bio/Technology, vol. 9, Jul. 1991, pp. 630–634.*
U.S. Appl. No. 08/955,638, filed Oct. 3, 1997, D'Amato.
U.S. Appl. No. 09/107,578, filed Feb. 24, 1997, D'Amato.
U.S. Appl. No. 09/300,202, filed Apr. 27, 1999, D'Amato.
U.S. Appl. No. 09/545,654, filed Apr. Apr. 10, 2000, D'Amato.
U.S. Appl. No. 09/547,087, filed Apr. 11, 2000, D'Amato.
U.S. Appl. No. 09/578,845, filed May 25, 2000, D'Amato.
U.S. Appl. No. 09/704,054, filed Nov. 1, 2000, D'Amato.
U.S. Appl. No. 09/710,534, filed Nov. 9, 2000, D'Amato.
U.S. Appl. No. 09/899,318, filed Jul. 5, 2001, D'Amato.
U.S. Appl. No. 09/899,344, filed Jul. 5, 2001, D'Amato.
U.S. Appl. No. 09/966,895, filed Sep. 28, 2001, D'Amato.
U.S. Appl. No. 10/001,183, filed Oct. 24, 2001, D'Amato.
U.S. Appl. No. 10/015,252, filed Dec. 12, 2001, D'Amato.
U.S. Appl. No. 10/020,391, filed Dec. 12, 2001, D'Amato.
U.S. Appl. No. 10/026,291, filed Dec. 20, 2001, D'Amato.
Phillips, G.D. et al, "Tumor Necrosis Factor—alpha (rh TNF) Fails to Stimulate Angiogenesis in the Rabbit Cornea" Anatomical Record, 1996 (May), 245 (1), pp. 53–56, abstract only.*

(Continued)

*Primary Examiner*—D. Margaret Seaman
(74) *Attorney, Agent, or Firm*—Jones Day

(57) ABSTRACT

The present invention comprises a group of compounds that effectively inhibit angiogenesis. More specifically, thalidomide and various related compounds such as thalidomide precursors, analogs, metabolites and hydrolysis products have been shown to inhibit angiogenesis. Importantly, these compounds can be administered orally.

1 Claim, 5 Drawing Sheets

OTHER PUBLICATIONS

Montrucchio, G. et al, "Tumor Necrosis Factor—alpha Induced Angiogenesis depends on in situ Platlet–Activating Gactor Biosynthesis" J. Exp. Med. 1994(Jul. 1), 180(1), pp. 377–382, abstract only.*
Hu, D.E. et al, "Inhibition of Angiogenesis in Rats by IL—1 Receptor Antagonist and Selected Cytokine Antibodies" Inflammation, 1994(Feb.), 18(1), pp. 45–58, abstract only.*
Fajardo, L.F. et al, "Dual Role of Tumor Necrosis Factor—alpha in Angiogenesis" Am. J. Pathol. 1992(May), 140(3), pp. 539–544, abstract only.*
Fabro, S. et al., "Teratogenic Activity of Thalidomide and Related Compounds," *Life Sciences,* 3:987–992 (1964).*
Shealy et al., "D–and L–Thalidomide," *Chem. and Indus.,* pp. 1030–1031 (Jun. 12, 1965).*
Folkman, "Tumor Angiogenesis: Therapeutic Implications," *The New England Journal of Medicine,* 285(21):1182–1186 (Nov. 18, 1971).*
Jonsson, N. Ake et al., "Chemical Structure and Texatogenic Properties," *Acta Pharm. Succica,*9:521–542, 431–446, 543–562 (1972).*
Eriksson, Sven O., "Synthesis and Alkaline Hydrolysis of some N–substituted Phthalimides," *Acta Pharm. Sucecica,* 10:63–74 (1973).*
Gimbrone et al., "Tumor Growth and Neovascularization: An Experimental Model Using the Rabbit Cornea," *J. Nat'l Cancer Institute,* 52(2):413–419 (1974).*
Fickenstcher, K., "Stereochemical Properties and Teratogenic Activity of Some Tetrahydrophthalimides," *Mol. Pharmacology,* 13:133–141 (1977).*
Knighton et al., "Avascular And Vascular Phases Of Tumor Growth In The Chick Embryo," *Br. J. Cancer*, 35:347–356 (1977).*
Blaschke, "Chromatographic Separation of Racemie Thalidomide and Teratogenic Activity of its Entantiomers (Chromatographische Racemattrennung von Thalidomid und teratogene Wirkung der Enantiomere)," *Drug Research,* 29 (II/10): 1640–1642 (1979). (English lang. summary on first page).*
Muthukkaruppan et al., "Angiogenesis in the Mouse Cornea, "*Science,* 205:1416–1418 (Sep. 28, 1979).*
Waters, et al., "Treatment of Ulcerative Colitis with Thalidomide," *British Medical Journal,* p. 792 (Mar. 24, 1979).*
Flohe et al., "Studies on the Hypothetical Relationship of Thalidomide–induced Embryopathy and Collagen Biosynthesis," *Arznetmittelforschung* (*Germany, West*) 31(2):315–20 (1981).*
Helm, *Drug Research,*31(I/6):941–949 (1981).*
Taylor et al., *Nature,* 297: p. 307 (1982).*
Belambe et al., "Should Thalidomide be Rehabilitated?," *Sem. Höp. Paris,* 59(45):3101–3104 (Dec. 8, 1983).*
Folkman et al., *Science,* 221:p. 719 (1983).*
Hendler, Sheldon S. et al., "Thalidomide for Autoimmune Disease," *Medical Hypothesis,* 10:437–443 (1983).*
Crum et al., *Science,* 230: 1375 et seq. (1985).*
Koch H.P. et al., "Thalidomide and Cogeners as Anti–inflammatory Agents," *Progress in Medicinal Chemistry,* 22:166–242 (1985).*
Sidky et al., *Cancer Research,* 47:pp. 5155–5161 (1987).*
Srivastava et al., "The Prognostic Significance of Tumor Vascularity in Intermediate–Thickness Skin Melanoma," *Am. J. Pathol,* 133:419–423 (1988). (abstract from MEDLINE:Accession No. 06745734).*
Chen et al., "Plasma Pharmacokinetics and Urinary Excretion of Thalidomide After Oral Dosing in Healthy Male Volunteers," *Drug Metabolism and Disposition,* 17(4):402–405 (1989).*
White et al., *New England J. Med.,* 320: pp. 1197–1200 (1989).*
Folkman et al., "Induction of Angiogenesis During the Transition from Hyperplasia to Neoplasia," *Nature,* 339:58–61 (May 4, 1989).*
"Thalidomide," *The Merck Index,* Eleventh Edition, Budavari et al., eds., Merck & co. New Jersey, p. 9182 (1989).*
Eger, K. et al., "Synthesis, Central Nervous System Activity and Teratogenicity of a Homothalidomide," *Arneim.–Forsch/Drug Res.,40*(IL Nr. 10):1073–1075 (1990).*
Ingber et al., "Synthetic Analogs Of Fumagillin That Inhibit Angiogenesis And Supress Tomour Growth," *Nature,* 348:555–557 (Dec. 6, 1990).*
Brem et al., *Neurosurg.,* 74:441–446 (1991).*
Matsuyama, Toshifumi, "Cytokines and HIV infection: is AIDS a Tumor Necrosis Factor Disease?," *AIDS,* 5(12):1405–1417 (1991).*
Weidner et al., "Tumor Angiogenesis and Metastasis—Correlation in Invasive Breast Carcinoma," *N.E.J. Med.,* 324(1):1–8(1991).*
Colville–Nash et al., "Angiogenesis and Rheumaoid Arthritis: Pathogenic and Therapeutic Implications", *Ann. Rheum. Dis.,* 51:919–925 (1992).*
Folkman and Shing, "Angiogenesis," *J. Biol. Chem.,* 267(16):10931–10934 (1992).*
Schweigerer and Fotsis, "Angiogenesis and angiogenesis inhibitors in paediatric diseases," *Eur. J. Pediatr.* 151:472–476 (1992).*
Torry and Rongish, "Angiogenesis in the Uterus: Potential Regulation and Relation to Tumor Angiogenesis," *Am. J. Reprod. Immunol.,* 27:171–179 (1992).*
Vogelsang et al., "Thalidomide for the Chronic Graft–Versus–Host Disease," *New England Journal of Medicine,* 326:1055–1058 (1992).*
Weidner et al., "Angiogenesis in Prostate Carcinoma," *Am. J. Path.,* 143(2):401–409 (1993).*
D'Amato et al., "Thalidomide is an Inhibitor of Angiogenesis," *PNAS USA,* 91:4082–4085 (1994).*
Oikawa et al., "Eponemycin, A Novel Antibiotic, is a Highly Powerful Angiogenesis Inhibitor," *Biochem. Biophys. Res. Comm.,*181(3)1070–1076 (Dec. 31, 1991).*
Otsuka et al., "A New Potent Angiogenesis Inhibitor, FR–118487," *J. Micro. Biotech.,* 1(3):163–168 (1991).*
De, A.U. et al., J. Pharm. Sci., 1975, 64(2), pp. 262–266.*
Gutierrez–Rodriguez, O. et al., J. Rheumatol. 1989, 16(2), pp. 158–163.*
Hatfill, S.J. et al., Leuk. Res. 1991, 15(2–3), pp. 129–136.*
Goihman–Yahr, M. et al., Int. Arch. Allergy Appl. Immunnol. 1978, 57(4), pp. 317–332.*
Mummery, C.L., et al., Toxicol. Lett. 1983, 18(3), pp. 201–209.*

* cited by examiner

METHODS FOR INHIBITION OF ANGIOGENESIS WITH A COMPOSITION COMPRISING 3-HYDROXYTHALIDOMIDE

Matter enclosed in heavy brackets [ ] appears in the original patent but forms no part of this reissue specification; matter printed in italics indicates the additions made by reissue.

CROSS-REFERENCE TO RELATED APPLICATION

This is a continuation of application Ser. No. 08/168,817, filed Dec. 15, 1993, now U.S. Pat. No. 5,629,327 which is a continuation-in-part of U.S. patent application Ser. No. 08/025,046, filed Mar. 1, 1993, now abandoned.

TECHNICAL FIELD

The present invention relates to methods and compositions for preventing unwanted angiogenesis in a human or animal. More particularly, the present invention relates to a method for preventing unwanted angiogenesis, particularly in angiogenesis dependent or associated diseases, by administration of compounds such as thalidomide and related compounds.

BACKGROUND OF THE INVENTION

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometdum and placenta. The control of angiogenesis is a highly regulated system of aniogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Aniogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A, deficiency, contact lens overwear, stopic keratitis, superior limbic keratitis, pterygium keratitis sioca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uvetitis/vitritis, mycobacterial infections, Lyme's disease, systemic lupus erythematosis, retinopathy of prematurity, Hales disease, Bechets disease, infections causing a retinitis or choroiditis, presumed ocular histoplasmosis, Bests disease, myopia, optic pits, Stragarts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Chrohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telanglectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastomas, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows minor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the bastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., Nature 297:307 (1982). The toxicity of protamine limits its practical use as a therapeutic. Folkman et al. have disclosed the use of heparin and seteroids to control angiogenesis. See Folkman et al., Science 221:719 (1983) and U.S. Pat. Nos. 5,001,116 and 4,994,443. Steroids, such as tetrahydrocortisol, which lack gluco and mineral cortidoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon α or human interferon β has been shown to inhibit tumor-induced angiogenesis in mouse dermis stimulated by human neoplastic cells. Interferon β is also a potent inhibitor of angiogenesis induced by allogeneic spleen cells. See Sidky et al., Cancer Research 47:5155–5161 (1987). Human recombinant α interferon (alpha/A) was reported to be successfully used in the treatment of pulmonary hemangiomatosis, an angiogenesis-induced disease. See White et al., New England J. Med. 320:1197–1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A 1.

PCT Application No. WO 92/14455 to Kaplan et al. is directed to a method for controlling abnormal concentration to TNF-α by administering thalidomide or thalidomide derivatives to a patient with toxic concentrations of TNF-α.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage cold be distributed in a form that the patient could self-administer.

SUMMARY OF THE INVENTION

In accordance with the present invention, compositions and methods are provided that are effective in inhibiting unwanted angiogenesis. These compositions are easily administered by different routes including oral and can be given in dosages that are safe and provide angiogenic inhibition at internal sites. The present invention provides a method of treating mammalian diseases mediated by undesired and uncontrolled angiogenesis by administering a composition comprising an anti-angiogenic compound in a dosage sufficient to inhibit angiogenesis.

The present invention also includes angiogenic inhibiting compounds that contain an epoxide group. These angiogenic inhibiting compounds can be administered to a human or animal alone or with epoxide hydrolase inhibiting compounds.

The present invention is especially useful for treating certain ocular neovascular diseases such as macular degeneration. The compounds which are contemplated as part of the present invention preferably can be given orally to the patient and thereby halt the progression of the disease. Other disease that can be treated using the present invention are diabetic retinopathy, neovascular glaucoma and retrolental fibroplasia.

Accordingly, it is an object of the present invention to provide a compound and method to inhibit unwanted angiogenesis in a human or animal.

It is yet another object of the present invention to provide a composition of inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases.

It is another object of the present invention to provide a method and composition for the treatment of diabetic retinopathy.

Other features and advantages of the invention will be apparent from the following description of preferred embodiments thereof.

These and other objects, features and advantages of the present invention will become apparent after a review of the following detailed description of the disclosed embodiments and the appended claims.

A)

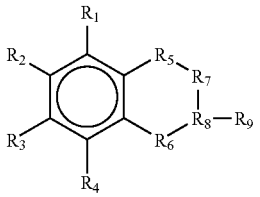

B)

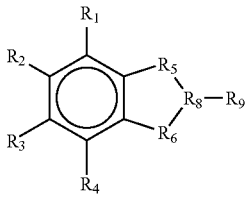

C)

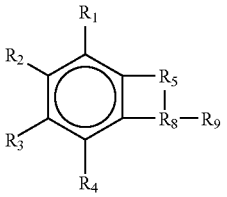

Figure 4:
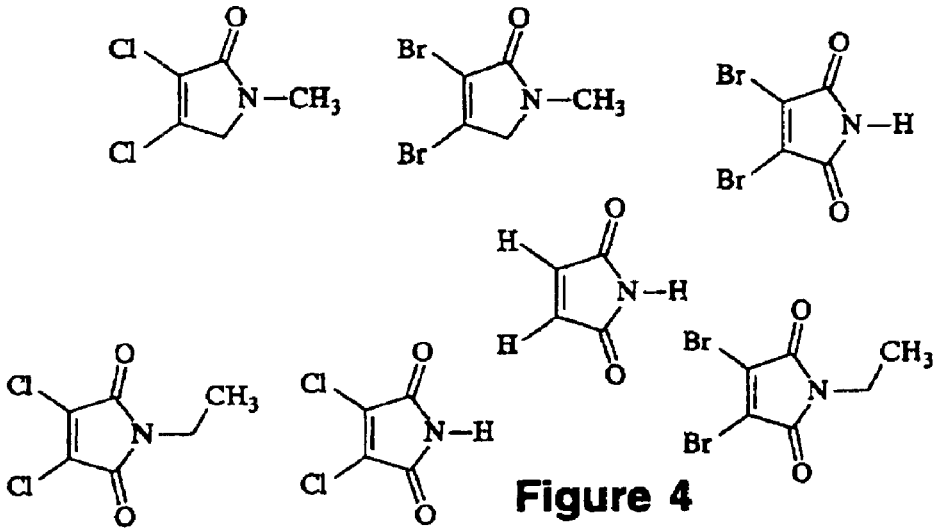

FIG. 4 is a listing of representative compounds in the genus represented by the following general formula:

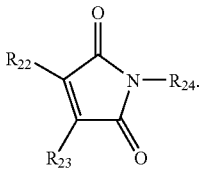

Figure 5:
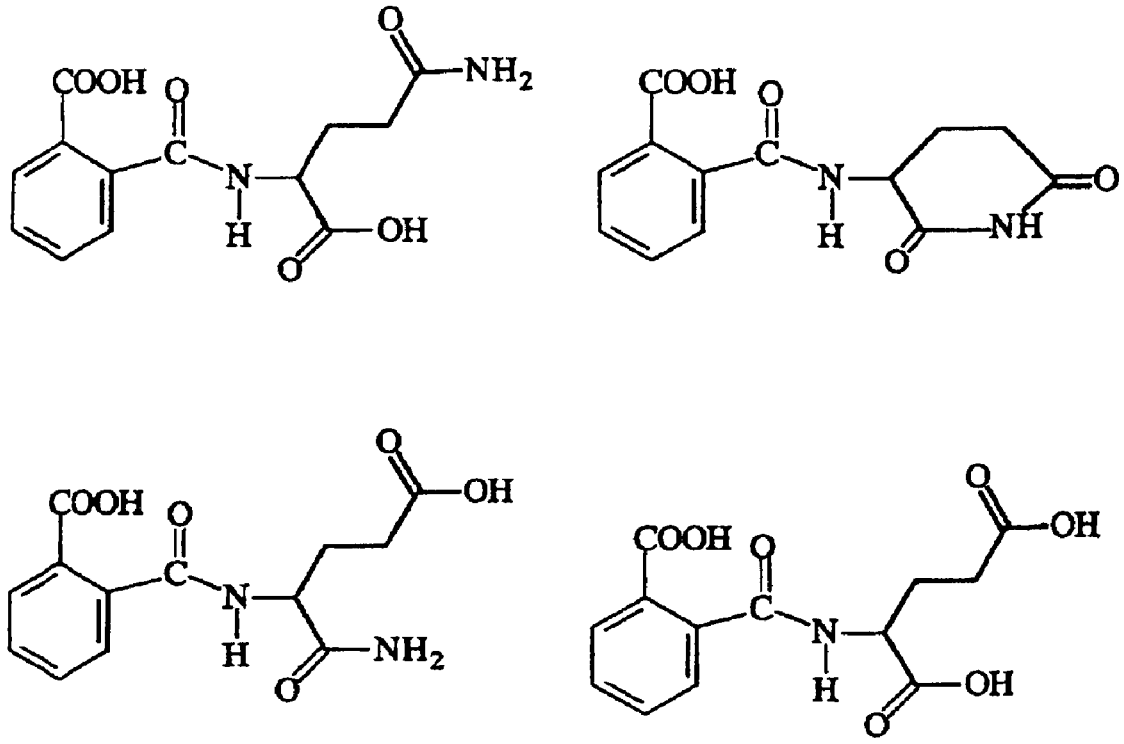

FIG. 5 is a listing of representative compounds in the genus represented by the following general formula:

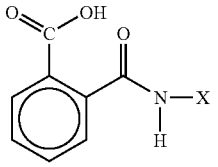

Figure 6:
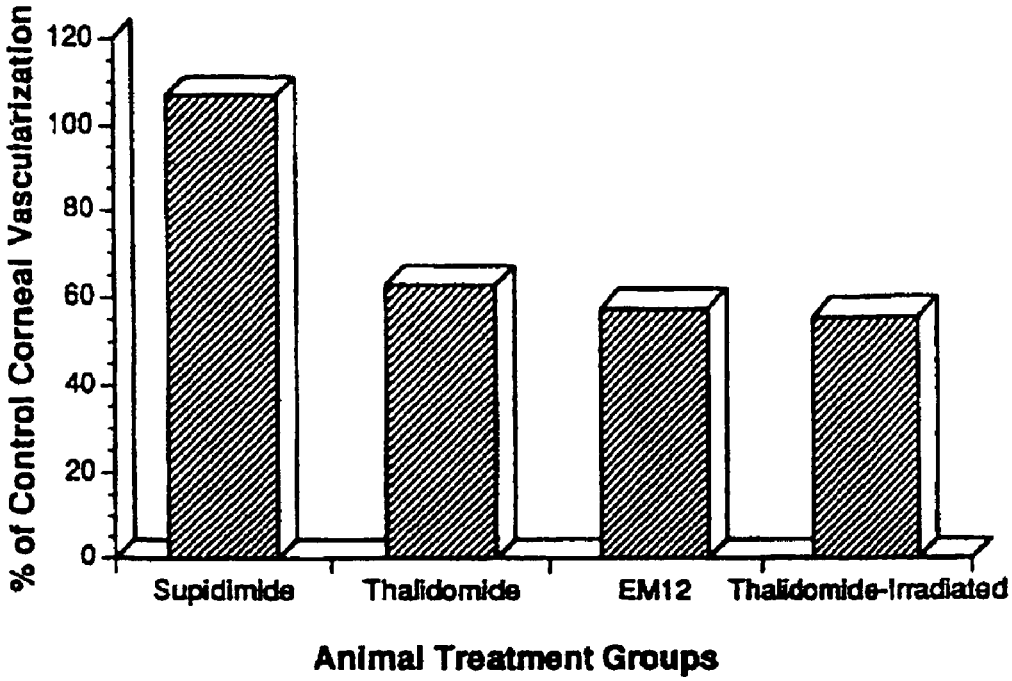

FIG. 6 shows the effect of thalidomide and EM12 on angiogenesis in a rabbit cornea model of angiogenesis.

Figure 7:
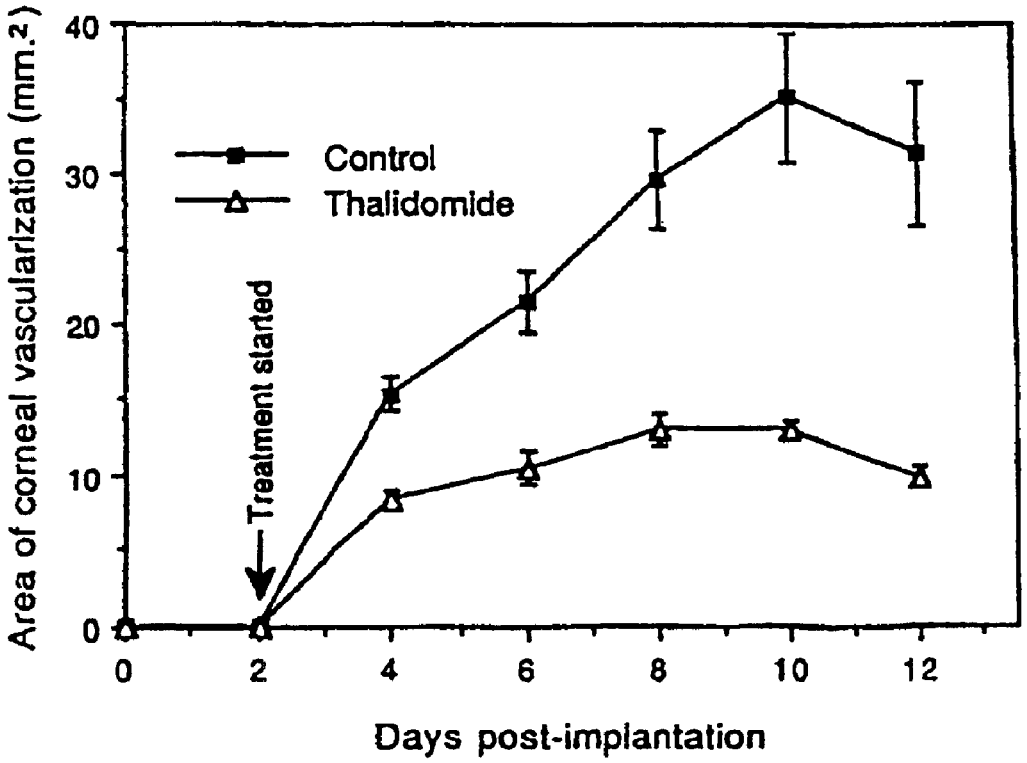

FIG. 7 shows the effect of thalidomide of the area of corneal vascularization in a rabbit cornea model of angiogenesis.

DETAILED DESCRIPTION

The present invention includes compositions and methods for the treatment of diseases that are mediated by angiogenesis. One embodiment of the present invention is the use of thalidomide or the metabolites of thalidomide as disclosed herein to inhibit unwanted angiogenesis. The present invention also includes compounds which cause dysmelia is the developing fetus and have anti-angiogenic activity. The present invention comprises a method of treating undesired angiogenesis in a human or animal comprising the steps of administering to the human or animal with the undesired angiogenesis a composition comprising an effective amount of a teratogenic compound that is anti-angiogenic.

Compounds that can be used in accordance with the present invention include compounds included in the following general formulae. Examples of compounds that have anti-angiogenic properties having one of the following three formulae (A), (B), or (C):

A)

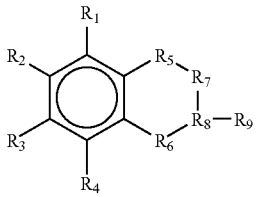

B)

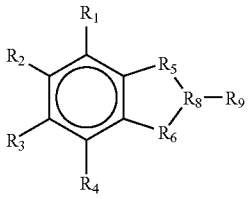

C)

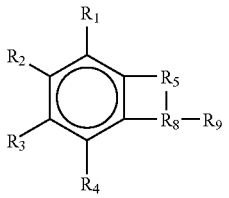

In the above formulae A), B), and C), $R_1$, $R_2$, $R_3$ and $R_4$ can be selected from: —H, —OH; =O, straight chained and branched alkanes, alkenes, alkynes; cyclic alkanes, alkenes, and alkynes; combinations of cyclic and acyclic alkanes, alkenes, and alkynes; alcohol, aldehyde, ketone, carboxylic acid, ester, or ether moieties in combination with acyclic, cyclic, or combination acyclic/cyclic moieties; aza; amino; $—XO_n$ or $—O—XO_m$, [where X=N and n=2; X=S and n=2 or 3; or X=P and n=1–3]; and halogens; $R_5$, $R_6$ and $R_7$ are each independently selected from:

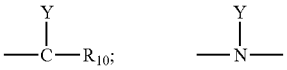

or —O— where Y is optional and is the same as defined above for $R_1$; and $R_{10}$ is the same as defined above for $R_1$, or (where Y is absent) $R_{10}$ is =O; and $R_8$ is independently selected from

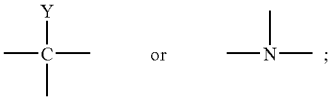

and $R_9$ is a moiety having formula D), E), F) G) or H):

D)

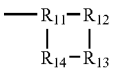

-continued

E)

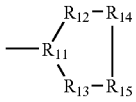

F)

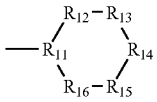

G)

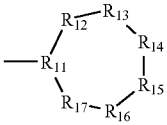

where each of $R_{12}$–$R_{17}$ is (independently) the same as defined above for $R_5$; and $R_{11}$ is independently the same as defined above for $R_8$;

H)

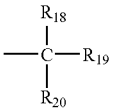

where $R_{18}$, $R_{19}$ and $R_{20}$ are independently selected from

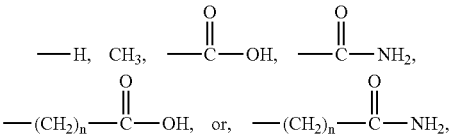

and n=1 to 4.

Accordingly, another aspect of the present invention features inhibiting angiogenesis in a mammal by administering a therapeutic composition comprising one of the above-described compounds in a dosage sufficient to inhibit angiogenesis.

Figure 1:
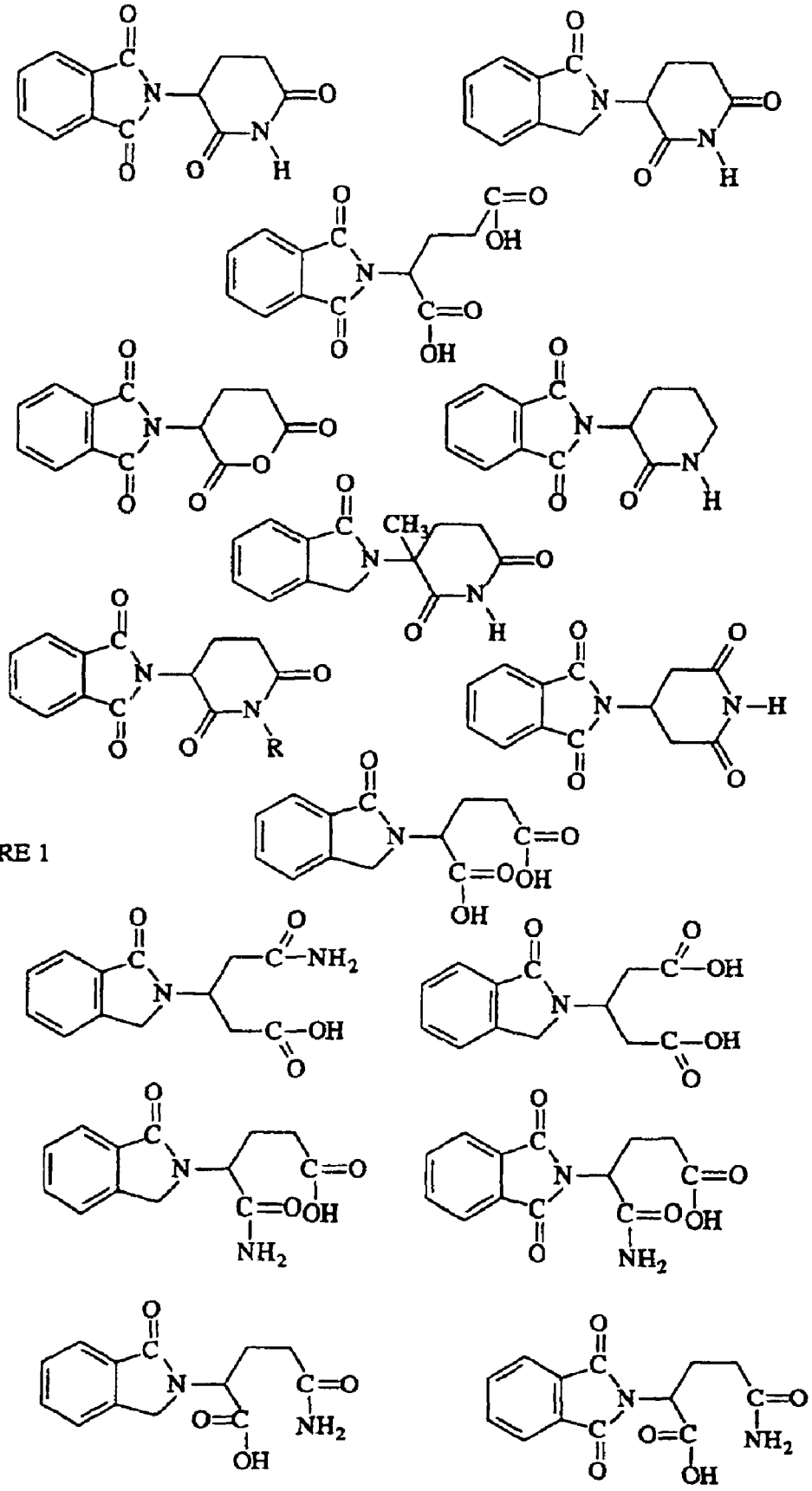
FIGS. 1 through 3 are a listing of representative compounds in the genus represented by the following general formulas.
Figure 2:
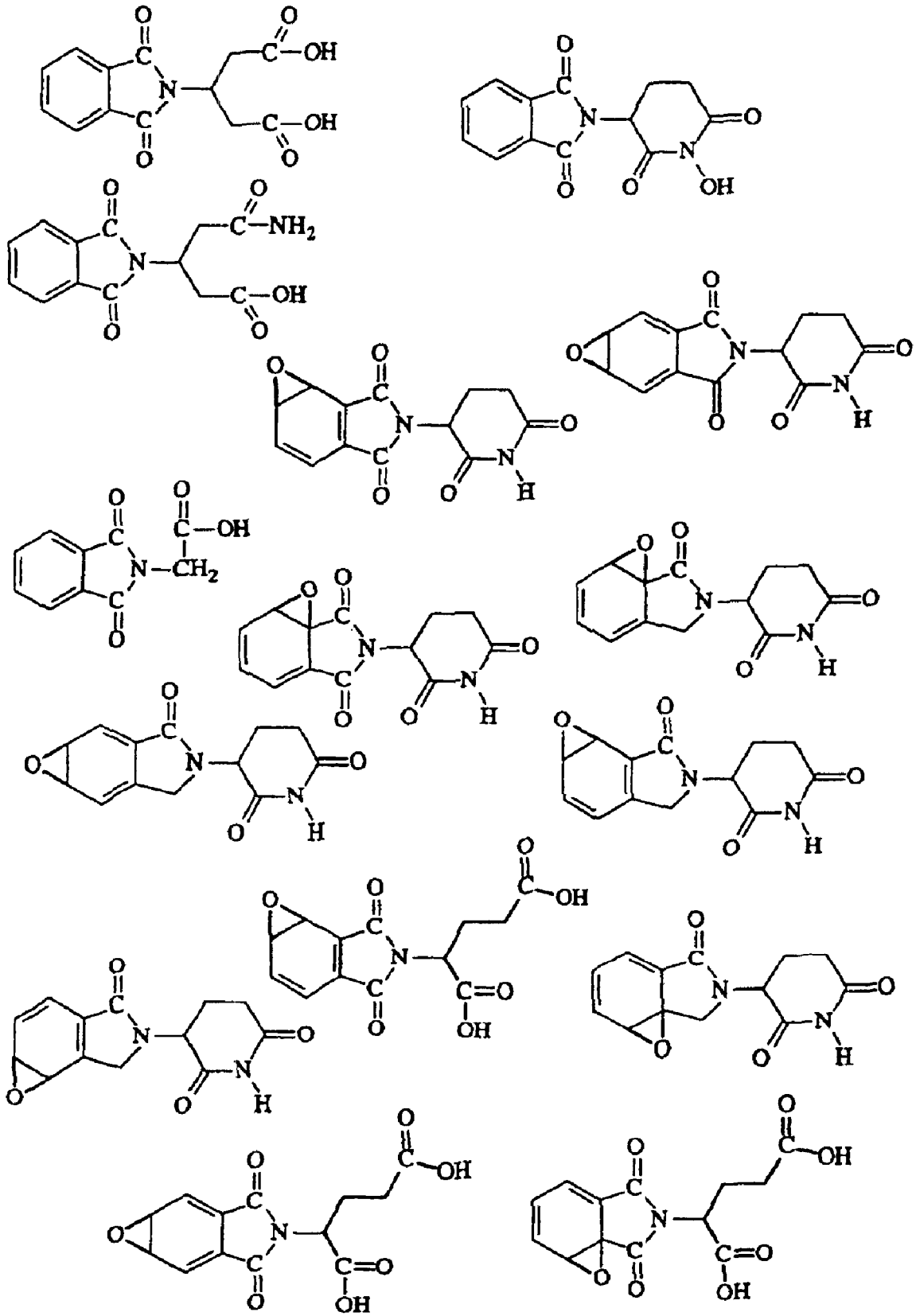
Figure 3:
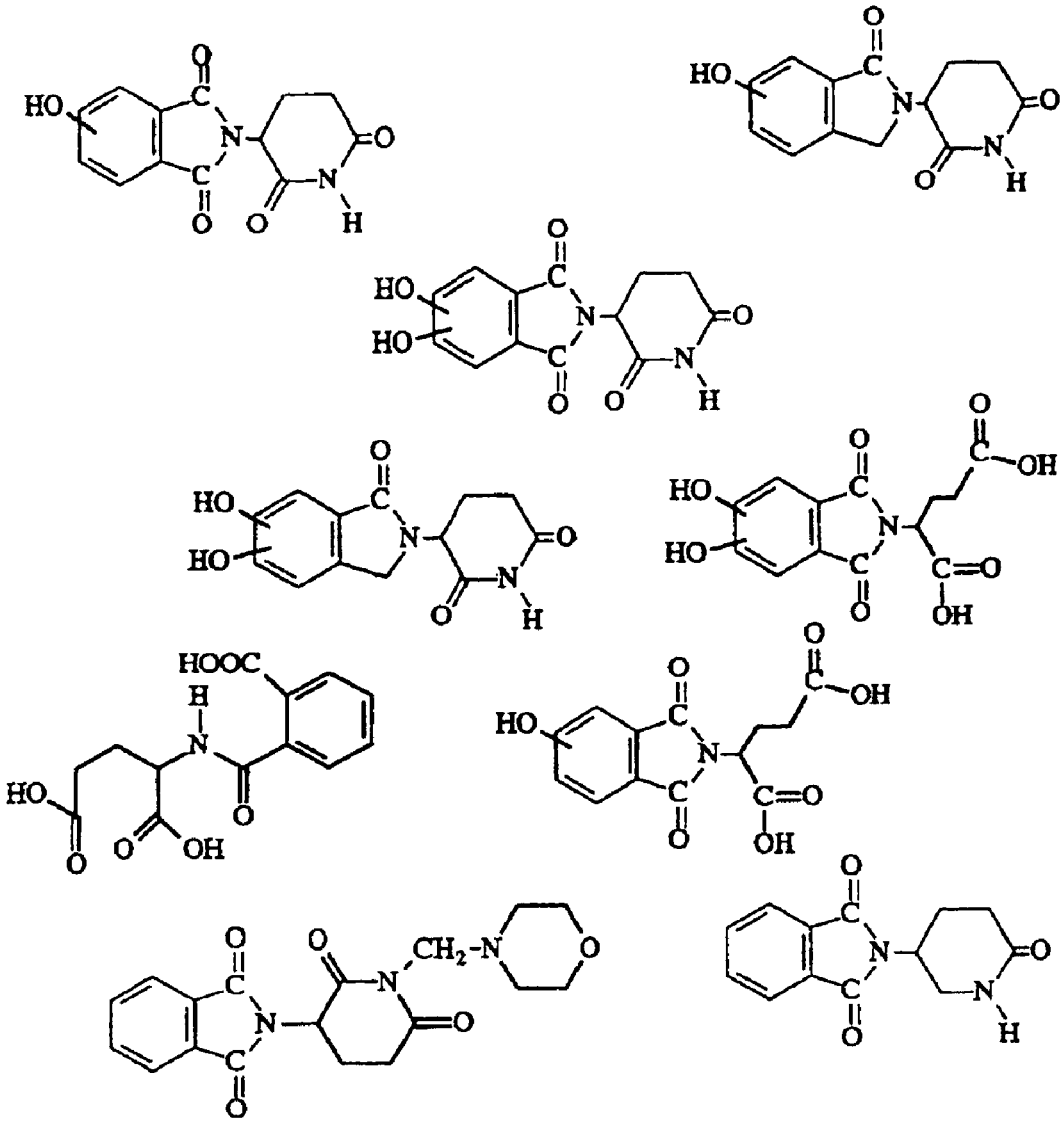

In preferred embodiments, the compound has formula B), where $R_5$ and $R_6$ are selected from the group consisting of:

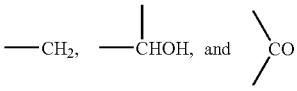

and $R_9$ has formula F) or H); and $R_{14}$ and $R_{16}$ are selected from the group consisting of:

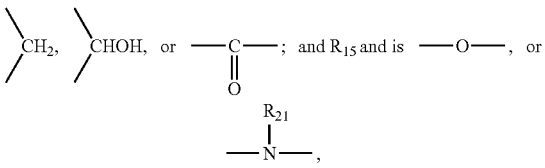

where $R_{21}$ is —H, $—CH_3$, or —OH. Specific preferred compounds according to this aspect of the present invention include thalidomide, its precursors, metabolites and analogs. Particular analogs include EM-12, N-phthaloly-DL-glutamic acid (PGA) or N-phthaloyl-DL-glutamine anhydride. Examples of compounds that are members of this genus are listed in FIGS. 1 through 3. It is to be understood that the compounds included as part of the present invention are not to be limited to those compounds shown in FIGS. 1 through 3 and include all other compounds that are members of the genus described by the general formulas herein.

Compounds of the following formula that have anti-angiogenic properties:

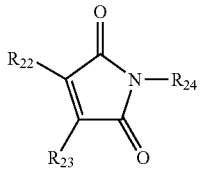

where $R_{22}$ and $R_{23}$ are (independently), —H, —F, —Cl, —Br, —I, —$CH_3$, or —$CH_2$—$CH_3$; and $R_{24}$ is —H, —$CH_3$, or —$CH_2$—$CH_3$.

The present invention also features inhibiting angiogenesis in a mammal by administering a compound according to the above formulae in a dosage sufficient to inhibit angiogenesis. Examples of specific compounds that are members of this genus are listed in FIG. 4.

Angiogenesis inhibition hydrolysis products of thalidomide having the following general formula can be used in practicing the present invention:

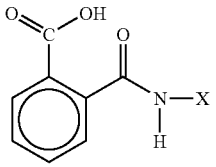

where X is $R_6$ as defined above, or

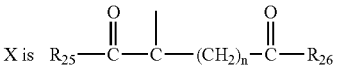

and $R_{25}$ and $R_{26}$ are, independently, —OH, —H, or $NH_2$, and n=1 through 4. Examples of such compounds are shown in FIG. 5.

Angiogenesis inhibition compounds having the following general formula can be used in practicing the present invention:

(I)

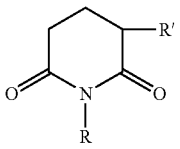

(II)

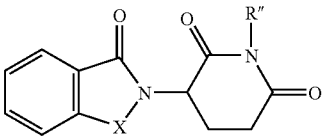

(a)

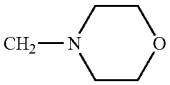

wherein compounds of structure (I), wherein R is selected from the group consisting of hydrogen, alkyl radicals of 1 to 6 carbon atoms, the phenyl radical, and the benzyl radical; and wherein R' is selected from the group consisting of the phthalimido radical and the succinimido radical and of structure (II), wherein X is $CH_2$ or C═O; R" is H, —$CH_2CH_3$, —$C_6H_5$, —$CH_2C_6H_5$, —$CH_2CH$═$CH_2$, or (a) and hydrolysis products of the compounds wherein R" is H and the piperidino ring or both the piperidino and the imido ring are hydrolyzed.

Another set of compounds that are considered part of the present invention are the epoxides of thalidomide, EM-12 and EM-138. Representative epoxide compounds are shown as follows:

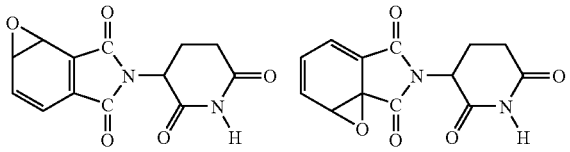

Epoxides of thalidomide

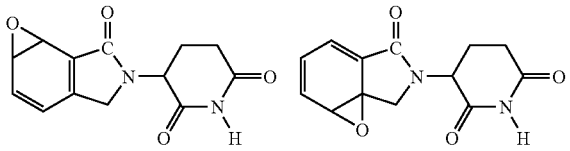

Epoxides of EM 12

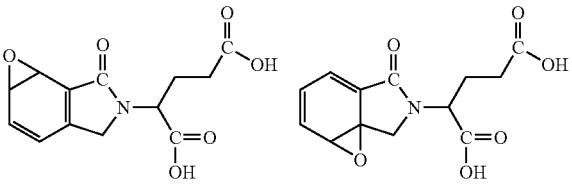

Epoxides of EM 138

It should be understood that the epoxide can be attached at the 6,1 site on the benzene ring, the 1,2 site, the 2,3 site 3,4 or the 4,5 site. All of these compounds are contemplated as part of the present invention.

The epoxides of the thalidomide, EM-12, and EM 138 can be hydrolyzed to the following compounds:

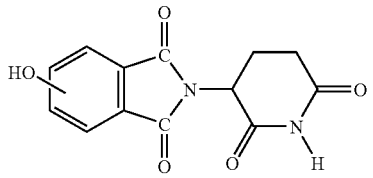

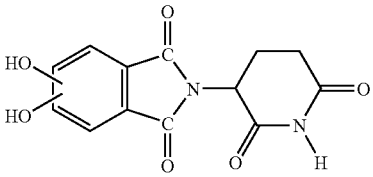

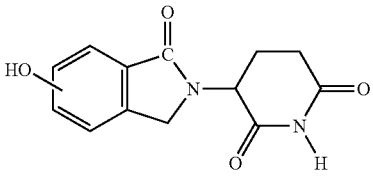

-continued

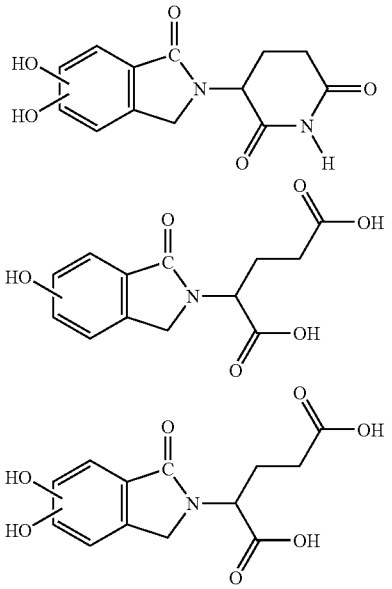

It is to be understood that the hydroxyl group can be on carbons 1, 2, 3, 4, 5 and 6 of the benzene ring. Also contemplated as part of the present invention are dihydroxyl compounds wherein the two hydroxyl groups are located bis to each other on carbons 1, 2, 3, 5 and 6 of the above compounds. The epoxides, the hydrolysis products of the epoxides, and the hydrolysis products of the thalidomide are all contemplated to be part of the present invention.

It is known that epoxides are hydrolyzed by a group of enzymes known as epoxide hydrolases. There is a class of compounds which are epoxide hydrolase inhibitors. Examples of these compounds are valpromide (2-propylpentanamide) and valproic acid (2-propylpentanoic acid). Becuase epoxides are important angiogenesis inhibitors, it is contemplated as part of the present invention, compositions comprising any of the angiogenesis inhibitors compounds recited herein in combination with epoxide hydrolase inhibitors. The epoxide hydrolase inhibitors can be administered to a human or animal together or sequentially. The epoxide group appears to be an important substituent common to several angiogenesis inhibitors. The use of epoxide hydrolase inhibitors to potentiate the activity of any angiogenesis inhibitor containing an epoxide is contemplated as part of the present invention. For example, the epoxide hydrolase inhibitors can be administered with the following epoxide-containing anti-angiogenesis compounds: AGM 1470, Eponimycin, microbial metabolites of Scolecobasidium arenarium designated f/2015, fr/111142 and fr/18487. See Olkawa, Biochem Biophys. Res. Comm, Vol. 81:1070 (1971) and Otsuka, J. Microbial. Biotech., Vol. 1:163 (1991).

It is contemplated as an embodiment of the present invention the use of the epoxide containing angiogenesis inhibitors with or without epoxide hydrolase inhibitors as a treatment for diseases mediated by elevated or toxic levels of TNF-α. TNF-α has been recognized as manifesting a dose dependent toxicity. If present at low levels for a long period of time, TNF-α can result in cachexia. Cachexais is a general weight loss and wasting occurring in the course of some chromic diseases such as cancer, opportunistic infections of AIDS, inflammatory diseases, parasitic diseases, tuberculosis, and high dose IL-2 therapy. The epoxide containing angiogenesis inhibitors, with or without epoxide hydrolase inhibitors, are also effective in treating diseases such as septic shock, leprosy and graph vs. host disease.

Other embodiments are within the present invention. For example, other dysmelia-causing compounds can be used according to the present invention, e.g. 4-methylphthalic acid, pyridoxine, vasopressin, acetazolamide, or a compound having the following formula (where R═H, —OH, or —$CH_3$):

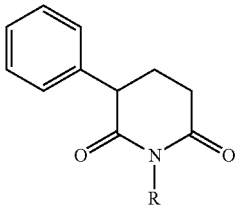

Other compounds which are teratogens, such as valproic acid (2-propylpentanoic acid), the retinoids, such as cis-retinoic acid, and rifampin may also be used in accordance with the invention.

In summary, the preferred compounds are thalidomide, as well as analogs, hydrolysis products, metabolites and precursors of thalidomide that are teratogenic, and, more specifically, that cause dismelia. However, it is to be understood that it is necessary for a compound to have both teratogenic activity and angiogenesis inhibiting activity to be considered part of the present invention. Dysmelia-causing compounds can be identified by the general procedures of Helm, Arzneimittleforschung, 31(i/6):941–949 (1981), in which rabbit pumps are examined after exposure to the compound in utero. The compounds can generally be purchased, e.g., from Andrulis Pharmaceuticals, Beltsville, Md., or synthesized according to known procedures. It is to be understood that the compounds of the present invention can exist as enantiomers and that the racemic mixture of enantiomers or the isolated enantiomers are all considered as within the scope of the present invention.

Many of the compounds that are contemplated as part of the present invention can be enriched in optically active enantiomers of the compounds specified above. Specifically, Blaschke has reported that the S enantiomers may be disproportionately responsible for the dismelia-producing effect of these compounds. See, generally Blaschke, Arzneimittelforschung 29:1640–1642 (1979). The above described articles generally describe procedures to obtain optically active preparations of the compounds of interest. See, e.g. Shealy et al., Chem. Indus. 1030 (1965); and Casini et al., Farmaco Ed. Sci. 19:563 (1964).

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combination may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., J. Neurosurg. 74:441–446 (1991).

The dosage of the compound will depend on the condition being treated, the particular compound, and other clinical factors such as weight and condition of the human or animal and the route of administration of the compound. It is to be understood that the present invention has application for both human and veterinary use. For oral administration to humans, a dosage of between approximately 0.1 to 300 mg/kg/day, preferably between approximately 0.5 and 50 mg/kg/day, and most preferably between approximately 1 to 10 mg/kg/day, is generally sufficient.

The formulations include those suitable for oral, rectal, ophthalmic, (including intravitreal or intrameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredients to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the same manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for pareteral administration include aqueous and non-aqueous sterile injection solutions which may contain anti-oxidants, buffers, bacteriostats and solutes which render the formulation isotomic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formualtions are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pteryglum keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

Disease associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uvetitis/vitritis, myobacterial infectants, Lyme's disease, systemic lupus erythematosis, retinopathy of prematurity, Eales disease, Bechets disease, infectants causing a retinitis or chroiditis, presumed ocular hisotplasmosis, Bests disease, myopia, optic pita, Stragarts disease, para planitis, chronic retinal detachment, hyperviscosity syndromes, toxoplasmosisi, trauma and post-laser complications. Other diseases include, but are not limited to, diseases associated with rubesoiss (neovascularization of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. It is believed that the blood vessels in the synovial lining of the joints undergo angiogenesis. In addition to forming new vascular networks, he endothelial cells release factors and reactive oxygen species that lead to pannus growth and cartilage destruction.

The factors involved in angiogenesis may actively contribute to, and help maintain, the chronically inflamed state of rheumatoid arthritis.

Another disease that can be treated according to the present invention are hemangiomas, Osler-Weber-Rendu disease, or hereditary hemorrhage, telangiectasia, solid or blood borne tumors are acquired immune deficiency syndrome.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The chick embryo chorioallantoic membrane assay described by Crum et al., Science 230:1375 et seq. (1985), is used to identify compounds that do not require further metabolic conversion. See also, U.S. Pat. No. 5,001,116, hereby incorporated by reference, which describes the CAM assay at col. 7 of the patent. Briefly, fertilized chick embryos are removed from their shell on day 3 or 4, and a methylcellulose disc containing the compounds is implanted on the chorioallantoic membrane. The embryos are examined 48 hours later and, if a clear avascular zone appears around the methylcellulose disc, the diameter of that zone is measured.

EXAMPLE II

Rabbit Cornea Angiogenesis Assay

Pellets for implantation into rabbit corneas were made by mixing 110 μl of saline containing 12 μg of recombinant bFGF (Takeda Pharmaceuticals-Japan) with 40 mg of sucralfate (Bukh Meditec-Denmark); this suspension was added to 80 μl of 12% hydron (Interferon Sciences) is ehtanol. 10 μl aliquots of this mixture was then pipetted onto teflon pegs and allowed to dry producing approximately 17 pellets. A pellet was implanted into corneal micropockets of each eye of an anesthetized female New Zealand white rabbit, 2 mm from the limbus followed by topical application of erythromycin ointment onto the surface of the cornea. The animals were fed daily from 2 days post-implantation by gastric lavage with either drug suspended in 0.5% carboxymethyl cellulose or 0.5% carboxymethyl cellulose alone. Thalidomide was purchased from Andrulus Pharmaceutical (Maryland) and the EM-12 and Supidinide were kindly provided by Grunenthal GMBH (Germany). The animals were examined with a slit lamp every other day in a masked manner by the same corneal specialist. The area of corneal neovascularization was determined by measuring with a reticulate the vessel length (L) from the limbus and the number of clock hours (C) of limbus involved. A formula was used to determine the area of a circular band segment $C/12*3.1416\,[r^3-(r-L)^2]$ where r=6 mm the measured radius of the rabbit cornea. Various mathematical models were utilized to determine the amount of vascularized cornea and this formula was found to provide the most accurate approximation of the area of the band of neovascularization that grows towards the pellet.

It is important to note that the rabbit cornea assay is preferable because it will generally recognize compounds that are inactive per se but are metabolized to yield active compounds. Thalidomide related compounds, as shown below in Example III, are known to be teratogens and are candidates for use in the present invention.

EXAMPLE III

Inhibition of bFGF Induced Corneal Neovascularization by Thalidomide and Related Analog Expressed as Percent of Median Control On Day 8

Pellets containing bFGF and sucraflate were implanted into micropouches of both cornea of rabbits according to Example II. Vessel ingrowth into clear cornea from the limbus was first noted on day 2 and treatments (200 mg/kg orally) were begun on this day. The area of corneal neovascularization was measured from day 4 through day 12. Day 8 measurements were used for comparison between groups. No regression of vessels and near maximal neovascularization was seen at this time point. Statistical analysis was performed with ANOVA with ranked data to account for intraexperimental variations and to guard against a non-normal distribution of data (i.e. outliers) by utilizing a homoparametric method.

The compounds tested were as follows:

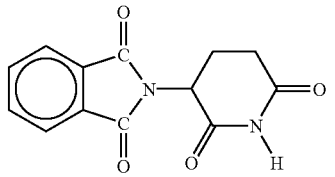

thalidomide

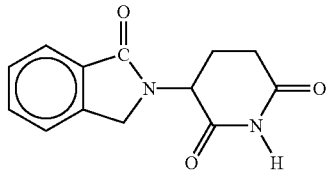

EM-12

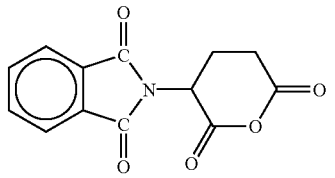

phthaloyl glutamic anhydride (PGA)

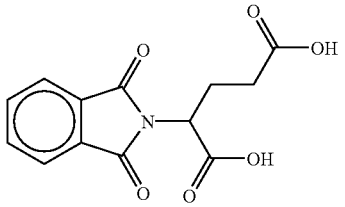

phthaloyl glutamic acid (PG Acid)

-continued

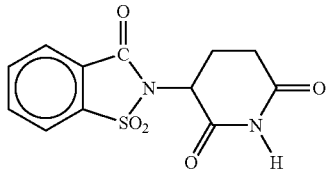

supidimide.

Treatment with a dose of (200 mg/kg) of thalidomide resulted in an inhibition of the area of vascularized cornea that ranged from 30–51% in three experiments with a media inhibition of 36% (FIG. 6) (n=30 eyes, p=0.0001, 2 way ANOVA with ranked data). The inibition of angiogenesis by thalidomide was seen after only two doses (FIG. 7). The rabbits did not demonstrate obvious sedation and there were no signs of toxicity or weight loss. The teratogenic analog EM-12, which shows the other properties of thalidomide was also inhibitory, with a mediation inhibition of 42% (p=10 eyes, p=0.002, 1-way ANOVA with ranked data). Supidimide, a nonteratogenic analog of thalidomide that retains the sedative properties of thalidomide, exhibited no activity (area 107% control, n=10 eyes, not statistically different from control). Other analogs, PGA and PG acid displayed weaker inhibitory effects than thalidomide (data not shown). The density of vessel ingrowth in thalidomide-treated animals was also markedly reduced.

EXAMPLE IV

EM-12 in Rabbit Cornea Assay

EM-12 was tested in the rabbit cornea assay described in Example II at 100 mg/kg/day and showed 21% inhibition, and at 200 mg/kg/day the assay showed 43% inhibition.

EXAMPLE V

Phthaloyl Glutamic Acid in CAM

Phthaloyl glutamic acid was tested in the above described CAM assay and exhibit an avascular zone with a mild scar.

EXAMPLE VI

Phthaloyl Glutamic Acids in Rabbit Cornea Activity

Phthaloyl glutamic acid described above at 200 mg/kg and exhibited 29% inhibition of angiogenesis.

EXAMPLE VII

Phthaloyl Glutamic Anhydride in CAM Assay

Phthaloyl glutamic anhydride was test in the CAM assay described above and exhibited an avascular zone.

It should be understood, of course, that the foregoing relates only to preferred embodiments of the present invention and that numerous modifications or alterations may be made therein without departing from the spirit and the scope of the invention as set forth in the appended claims.

I claim:

[1. A method of treating undesired angiogenesis in a human or animal comprising the step of administering to the human or animal with the undesired angiogenesis a composition comprising an effective amount of an angiogenesis-inhibiting compound selected from the group consisting of 3-amothalidomide, and 3-hydroxythalidomide, and metabolities or hydrolysis products of 3-aminothalidomide and metabolites or hydrolysis products of 3-hydroxythalidomide, and mixtures thereof.]

[2. The method of claim 1, wherein the undesired angiogenesis is associated with retinal neovascularization.]

[3. The method of claim 1, wherein the undesired angiogenesis is associated with choroidal neovascularization.]

[4. The method of claim 1 wherein the undesired angiogenesis is associated with diabetic retinopathy.]

[5. The method of claim 1, wherein the undesired angiogenesis is associated with macular degeneration.]

[6. The method of claim 1, wherein the undesired angiogenesis is associated with corneal neovascularization.]

[7. The method of claim 1 wherein the undesired angiogenesis occurs in retinopathy of prematurity.]

[8. The method of claim 1 wherein the undesired angiogenesis occurs in corneal graft rejection.]

[9. The method of claim 1 wherein the undesired angiogenesis occurs in neovascular glaucoma.]

[10. The method of claim 1 wherein the undesired angiogenesis occurs in retrolental fibroplasia.]

[11. The method of claim 1 wherein the undesired angiogenesis occurs in epidemic keratoconjunctivitis.]

[12. The method of claim 1 wherein the undesired angiogenesis occurs due to Vitamin A deficiency.]

[13. The method of claim 1 wherein the undesired angiogenesis occurs due to contact lens overwear.]

[14. The method of claim 1 wherein the undesired angiogenesis occurs in stopitc keratitis.]

[15. The method of claim 1 wherein the undesired angiogenesis occurs in superior limbic keratitis.]

[16. The method of claim 1 wherein the undesired angiogenesis occurs in pterygium keratitis sicca.]

[17. The method of claim 1 wherein the undesired angiogenesis occurs in sjogrens.]

[18. The method of claim 1 wherein the undesired angiogenesis occurs in acne rosacea.]

[19. The method of claim 1 wherein the undesired angiogenesis occurs in phylectemolosis.]

[20. The method of claim 1 wherein the undesired angiogenesis occurs in syhilis.]

[21. The method of claim 1 wherein the undesired angiogenesis occurs in Myobacteria infections other than leprosy.]

[22. The method of claim 1 wherein the undesired angiogenesis occurs in lipid degeneration.]

[23. The method of claim 1 wherein the undesired angiogenesis occurs in chemical burns.]

[24. The method of claim 1 wherein the undesired angiogenesis occurs in bacterial ulcers.]

[25. The method of claim 1 wherein the undesired angiogenesis occurs in fungal ulcers.]

[26. The method of claim 1 wherein the undesired angiogenesis occurs in Herpes simplex infections.]

[27. The method of claim 1 wherein the undesired angiogenesis occurs in Herpes zoster infections.]

[28. The method of claim 1 wherein the undesired angiogenesis occurs in protozona infections.]

[29. The method of claim 1 wherein the undesired angiogenesis occurs in Kaposi's sarcoma.]

[30. The method of claim 1 wherein the undesired angiogenesis occurs in Mooren ulcer.]

[31. The method of claim 1 wherein the undesired angiogenesis occurs in Terrien's marginal degeneration.]

[32. The method of claim 1 wherein the undesired angiogenesis occurs in marginal keratolysis.]

[33. The method of claim 1 wherein the undesired angiogenesis is caused by trauma.]

[34. The method of claim 1 wherein the undesired angiogenesis occurs in rheumatoid arthritis.]

[35. The method of claim 1 wherein the undesired angiogenesis occurs in systemic lupus.]

[36. The method of claim 1 wherein the undesired angiogenesis occurs in polyarteritis.]

[37. The method of claim 1 wherein the undesired angiogenesis occurs in Wegeners sarcoidosis.]

[38. The method of claim 1 wherein the undesired angiogenesis occurs in scleritis.]

[39. The method of claim 1 wherein the undesired angiogenesis occurs in Steven's Johnson disease.]

[40. The method of claim 1 wherein the undesired angiogenesis occurs in radial keratotomy.]

[41. The method of claim 1 wherein the undesired angiogenesis occurs in sickle cell anemia.]

[42. The method of claim 1 wherein the undesired angiogenesis occurs in sarcoid.]

[43. The method of claim 1 wherein the undesired angiogenesis occurs in pseudoxanthoma elasticum.]

[44. The method of claim 1 wherein the undesired angiogenesis occurs in Pagets disease.]

[45. The method of claim 1 wherein the undesired angiogenesis occurs in vein occlusion.]

[46. The method of claim 1 wherein the undesired angiogenesis occurs in artery occlusion.]

[47. The method of claim 1 wherein the undesired angiogenesis occurs in carotid obstructive disease.]

[48. The method of claim 1 wherein the undesired angiogenesis occurs in chronic uvetitis.]

[49. The method of claim 1 wherein the undesired angiogenesis occurs in chronic vitritis.]

[50. The method of claim 1 wherein the undesired angiogenesis occurs in Lyme's disease.]

[51. The method of claim 1 wherein the undesired angiogenesis occurs in Eales disease.]

[52. The method of claim 1 wherein the undesired angiogenesis occurs in Bechets disease.]

[53. The method of claim 1 wherein the undesired angiogenesis occurs in myopis.]

[54. The method of claim 1 wherein the undesired angiogenesis occurs in optic pits.]

[55. The method of claim 1 wherein the undesired angiogenesis occurs in Stargarts disease.]

[56. The method of claim 1 wherein the undesired angiogenesis occurs in pars planitis.]

[57. The method of claim 1 wherein the undesired angiogenesis occurs is chronic retinal detachment.]

[58. The method of claim 1 wherein the undesired angiogenesis occurs in hyperviscosity syndromes.]

[59. The method of claim 1 wherein the undesired angiogenesis occurs in toxoplasmosis.]

[60. The method of claim 1 wherein the undesired angiogenesis occurs in post-laser complications.]

[61. The method of claim 1 wherein the undesired angiogenesis occurs in abnormal proliferation of fibrovascular tissue.]

[62. The method of claim 1 wherein the undesired angiogenesis occurs in hemangiomas.]

[63. The method of claim 1 wherein the undesired angiogenesis occurs in Osler-Weber-Rendu.]

[64. The method of claim 1 wherein the undesired angiogenesis occurs in solid tumors.]

[65. The method of claim 1 wherein the undesired angiogenesis occurs in blood borne tumors.]

[66. The method of claim 1 wherein the undesired angiogenesis occurs in acquired immune deficiency syndrome.]

[67. The method of claim 1 wherein the undesired angiogenesis occurs in occular neovascular disease.]

[68. The method of claim 1 wherein the undesired angiogenesis occurs in osteoarthritis.]

[69. The method of claim 1 wherein the undesired angiogenesis occurs in diseases caused by chronic inflammation.]

[70. The method of claim 1 wherein the undesired angiogenesis occurs in Chron's disease.]

[71. The method of claim 1 wherein the undesired angiogenesis occurs in ulceritive colitis.]

[72. The method of claim 1 wherein the undesired angiogenesis occurs in the tumors of rhabdomyosarcoma.]

[73. The method of claim 1 wherein the undesired angiogenesis occurs in the tumors of retinoblastoma.]

[74. The method of claim 1 wherein the undesired angiogenesis occurs in the tumors of Ewing sarcoma.]

[75. The method of claim 1 wherein the undesired angiogenesis occurs in the tumors of neuroblastoma.]

[76. The method of claim 1 wherein the undesired angiogenesis occurs in the tumors of osteosarcoma.]

[77. The method of claim 1 wherein the undesired angiogenesis occurs in leukemia.]

[78. The method of claim 1 wherein the undesired angiogenesis occurs in psoriasis.]

[79. The method of claim 1 wherein the undesired angiogenesis occurs in atherosclerosis.]

[80. The method of claim 1 wherein the undesired angiogenesis occurs in pemphigoid.]

*81. A method of treating undesired angiogenesis in a human or animal comprising administering to the human or animal with the undesired angiogenesis a composition comprising an effective amount of 3-hydroxythalidomide, wherein the undesired angiogenesis is associated with retinal neovascularization, choroidal neovascularization, diabetic retinopathy, macular degeneration, corneal neovascularization, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sjorgrens, acne rosacea, phyletenulosis, syphilis, Mycobacteria infections other than leprosy, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, trauma, rheumatoid arthritis, systemic lupus, polyarteritis, Wegeners sarcoidosis, scleritis, Steven's Johnson disease, radial keratotomy, sickle cell anemia, sarcoid, pseudoxanthoma elasticium, Pagets disease, vein occlusion, artery occlusion, carotid obstructive disease, chronic uveitus, chronic vitritis, Lyme's disease, Eales disease, Bechets disease, myopia, optic pits, Stargarts disease, pars planitis, chronic retinal detachment, hyperviscosity syndromes, toxoplasmoisis, post-laser complications, abnormal proliferation of fibrovascular tissue, hemangiomas, Osler-Weber-Rendu disease solid tumors, blood borne tumors, acquired immune deficiency syndrome, ocular neovascular disease, osteoarthritis, Crohn's disease, ulcerative colitis, rhabdomyosarcoma, retinoblastoma, Ewing sarcoma, neuroblastoma, osteosarcoma, leukemia, psoriasis, atherosclerosis or pemphigoid.*

* * * * *